(12) United States Patent
Cheney

(10) Patent No.: US 9,408,647 B2
(45) Date of Patent: *Aug. 9, 2016

(54) METHOD AND APPARATUS FOR USE OF A COMPRESSING PLATE

(71) Applicant: BioMedical Enterprises, Inc., San Antonio, TX (US)

(72) Inventor: Daniel F. Cheney, San Antonio, TX (US)

(73) Assignee: BioMedical Enterprises, Inc., San Antonio, TX (US)

( * ) Notice: Subject to any disclaimer, the term of this patent is extended or adjusted under 35 U.S.C. 154(b) by 187 days.

This patent is subject to a terminal disclaimer.

(21) Appl. No.: 14/191,809

(22) Filed: Feb. 27, 2014

(65) Prior Publication Data

US 2015/0238238 A1    Aug. 27, 2015

(51) Int. Cl.
| | | |
|---|---|---|
| *A61B 17/88* | (2006.01) | |
| *A61B 17/80* | (2006.01) | |
| *A61B 17/064* | (2006.01) | |
| *A61B 17/17* | (2006.01) | |
| *A61B 17/90* | (2006.01) | |
| *A61B 17/00* | (2006.01) | |

(52) U.S. Cl.
CPC ........... *A61B 17/808* (2013.01); *A61B 17/0642* (2013.01); *A61B 17/1728* (2013.01); *A61B 17/80* (2013.01); *A61B 17/8004* (2013.01); *A61B 17/8085* (2013.01); *A61B 17/8872* (2013.01); *A61B 2017/00867* (2013.01); *A61B 2017/0645* (2013.01); *A61B 2017/90* (2013.01)

(58) Field of Classification Search
CPC ................. A61B 2017/00867; A61B 17/0642; A61B 2017/0645; A61B 17/1728; A61B 17/80; A61B 17/8004; A61B 17/808; A61B 17/8085; A61B 17/8872; A61B 2017/90
See application file for complete search history.

(56) References Cited

U.S. PATENT DOCUMENTS

| | | |
|---|---|---|
| 3,779,240 A | 12/1973 | Kondo |
| 3,866,607 A | 2/1975 | Forsythe |
| 3,939,828 A | 2/1976 | Mohr et al. |
| 4,408,601 A | 10/1983 | Wenk |
| 4,513,744 A | 4/1985 | Klaue |
| 5,634,926 A | 6/1997 | Jobe |
| 5,779,707 A | 7/1998 | Bertholet et al. |
| 5,785,713 A | 7/1998 | Jobe |
| 6,001,110 A | 12/1999 | Adams |
| 6,093,188 A | 7/2000 | Murray |
| 6,187,009 B1 | 2/2001 | Herzog et al. |
| 6,325,805 B1 | 12/2001 | Ogilvie et al. |
| 6,773,437 B2 | 8/2004 | Ogilvie et al. |
| 7,115,129 B2 | 10/2006 | Heggeness |
| 7,186,254 B2 * | 3/2007 | Dinh .................. A61B 17/7059 606/70 |
| 7,857,838 B2 | 12/2010 | Orbay |
| 7,867,265 B2 | 1/2011 | Beutter |

(Continued)

*Primary Examiner* — Larry E Waggle, Jr.
(74) *Attorney, Agent, or Firm* — Christopher L. Makay

(57) ABSTRACT

An orthopedic bone plate constructed from shape memory material provides the ability to move from an open shape to a compressed shape and create compression on two bones or bone fragments to encourage healing. The plate may be any number of shapes, with two or more screws anchoring the plate to bone. The plate is affixed to bone in a sequence of steps that involve first placing the plate on an insertion tool, attaching drill guide tubes, placing the plate over bone, drill holes in bone, and then attaching the plate to the bone via screws. The insertion tool can then be removed at the surgeon's convenience allowing compression on the two bones.

16 Claims, 16 Drawing Sheets

(56) References Cited

U.S. PATENT DOCUMENTS

| | | | |
|---|---|---|---|
| 7,931,679 B2 | 4/2011 | Heggeness | |
| 7,931,680 B2 | 4/2011 | Myerson | |
| 7,985,222 B2 * | 7/2011 | Gall | A61B 17/7225 606/60 |
| 7,993,380 B2 * | 8/2011 | Hawkes | A61B 17/7008 606/282 |
| 8,083,781 B2 * | 12/2011 | Reimels | A61B 17/8004 606/282 |
| 8,118,952 B2 | 2/2012 | Gall | |
| 8,167,918 B2 | 5/2012 | Strnad | |
| 8,172,886 B2 | 5/2012 | Castaneda et al. | |
| 8,226,693 B2 | 7/2012 | Reimels | |
| 8,231,625 B2 | 7/2012 | Graham | |
| 8,257,403 B2 | 9/2012 | Den Hartog | |
| 8,292,898 B2 * | 10/2012 | Castaneda | A61B 17/1728 606/101 |
| 8,348,980 B2 | 1/2013 | Prasad | |
| 8,535,355 B2 | 9/2013 | Prasad | |
| 8,574,270 B2 | 11/2013 | Hess | |
| 8,585,742 B2 | 11/2013 | Windolf | |
| 8,685,067 B2 | 4/2014 | King | |
| 8,728,127 B2 | 5/2014 | Stewart | |
| 8,828,063 B2 | 9/2014 | Blitz | |
| 8,882,815 B2 | 11/2014 | Bottlang | |
| 8,940,026 B2 | 1/2015 | Hilse | |
| 8,974,504 B2 | 3/2015 | Hess et al. | |
| 8,986,353 B2 | 3/2015 | Johnson | |
| 9,005,255 B2 | 4/2015 | Lewis | |
| 9,005,257 B2 | 4/2015 | Sun | |
| 2004/0034354 A1 | 2/2004 | Paul | |
| 2004/0260306 A1 | 12/2004 | Fallin et al. | |
| 2005/0085812 A1 | 4/2005 | Sherman et al. | |
| 2005/0085814 A1 | 4/2005 | Sherman et al. | |
| 2005/0187555 A1 | 8/2005 | Biedermann et al. | |
| 2005/0273108 A1 | 12/2005 | Groiso | |
| 2006/0235405 A1 | 10/2006 | Hawkes | |
| 2006/0293670 A1 | 12/2006 | Smisson, III et al. | |
| 2007/0225715 A1 | 9/2007 | Deffenbaugh et al. | |
| 2008/0097443 A1 | 4/2008 | Campbell | |
| 2009/0062800 A1 | 3/2009 | Shano | |
| 2009/0275947 A1 | 11/2009 | Graham et al. | |
| 2011/0178555 A1 | 7/2011 | Heggeness | |
| 2013/0026206 A1 | 1/2013 | Fox | |
| 2013/0026207 A1 | 1/2013 | Fox | |
| 2013/0030437 A1 | 1/2013 | Fox | |
| 2013/0030438 A1 | 1/2013 | Fox | |
| 2013/0206815 A1 | 8/2013 | Fox | |
| 2013/0231667 A1 | 9/2013 | Taylor et al. | |

* cited by examiner

METHOD AND APPARATUS FOR USE OF A COMPRESSING PLATE

BACKGROUND OF THE INVENTION

1. Field of the Invention

The present invention relates to compressing plates and more particularly but not by way of limitation to a method and apparatus for the use of compressing plates to assist in osteosynthesis.

2. Description of the Related Art

Wire, staple, and plate fixation of bone have been used clinically for decades. In the last 20 years or so, nickel-titanium and shape memory materials have been used in orthopedics for their shape changing and superelastic properties. Shape memory devices feature a martensitic and austenitic form, in which the addition of energy in the form of heat transforms the device from a temporary martensite state to a final austenite state at a defined temperature. The heat for transformation generally is categorized as being (1) room temperature activated (i.e. superelastic), (2) body temperature activated (i.e. body temperature), and (3) above body temperature activated (i.e. heated). The use of a shape memory plate, capable of transforming from a preliminary shape to a compressed final shape, presents unique challenges. If the plate is superelastic, then the plate is inclined to immediately transform at room temperature, making implantation and the use of screws difficult for a surgeon. If the plate is body temperature or heated, then the surgeon has to rely on either body heat, which is reduced during surgery due to the open wound, or an external heating source to transform the plate. For various reasons, many surgeons would prefer a superelastic shape memory plate.

Accordingly, an apparatus and a method of surgical use for a shape memory plate that restrains the plate in an open position while screws are attached and then releases the plate to compress the bones and assist with osteosynthesis would provide an improvement in compressing plate surgeries.

SUMMARY OF THE INVENTION

In accordance with the present invention, a fixation system includes a plate adapted for affixing between a first bone and a second bone and an insertion tool. The plate defines a central opening and is configurable between an open shape and a compressed shape. Once the plate has been moved to its open shape, the insertion tool inserts into the central opening and abuts the plate to retain the plate in its open shape. The insertion tool allows locating of the plate at the first bone and the second bone. After the plate has been affixed to the first and second bones, the insertion tool releases the plate allowing the plate to move from its open shape to its compressed shape, thereby compressing the first bone with the second bone.

The plate includes a first end portion defining a first screw hole and a second end portion defining a second screw hole. The plate further includes first and second arms disposed between the first and second end portions, such that the first and second end portions and the first and second arms define the central opening. The first and second arms expand to configure the plate in its open shape and contract to configure the plate in its compressed shape.

The insertion tool includes a retention spacer that inserts into the central opening of the plate when the plate is in its open shape such that the retention spacer abuts the first and second end portions of the plate to retain the plate in its open shape. The insertion tool further includes a platform having a first guide hole that aligns with the first screw hole and a second guide hole that aligns with the second screw hole when the plate is in its open shape.

The fixation system includes a first guide tube that inserts through the first guide hole of the platform and engages the first screw hole of the plate and a second guide tube that inserts through the second guide hole and engages the second screw hole of the plate. The fixation system also includes locating pins that insert through the first and second guide tubes for the purpose of creating pilot holes in the first and second bones. The locating pins further retain the plate at the first and second bones. The locating pins include marks that represent the depth of the locating pins within the first and second bones.

The plate pre-loaded on the insertion tool may be delivered in a sterile package. Likewise, the first and second guide tubes coupled with the plate may be delivered in the sterile package along with the plate pre-loaded on the insertion tool.

A first bone is affixed with a second bone as follows. A plate in its open shape couples with an insertion tool. A first drill guide tube engages a first screw hole of the plate, and a second drill guide tube engages a second screw hole of the plate. The insertion tool locates the plate onto first and second bones. A first locating pin inserts through the first drill guide tube and drills into the first bone. A second locating pin inserts through the second drill guide tube and drills into the second bone. The first locating pin removes from the first drill guide tube, and the first drill guide tube disengages from the plate. A first screw inserts through the first screw hole of the plate and into the first bone. The second locating pin removes from the second drill guide tube, and the second drill guide tube disengages from the plate. A second screw inserts through the second screw hole of the plate and into the second bone. The insertion tool decouples from the plate such that the plate moves to its compressed shape.

Other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

DETAILED DESCRIPTION OF THE PREFERRED EMBODIMENT

As required, a detailed embodiment of the present invention is disclosed herein; however, it is to be understood that the disclosed embodiment is merely exemplary of the invention, which may be embodied in various forms. It is further to be understood that the figures are not necessarily to scale, and some features may be exaggerated to show details of particular components or steps.

Figure 1:
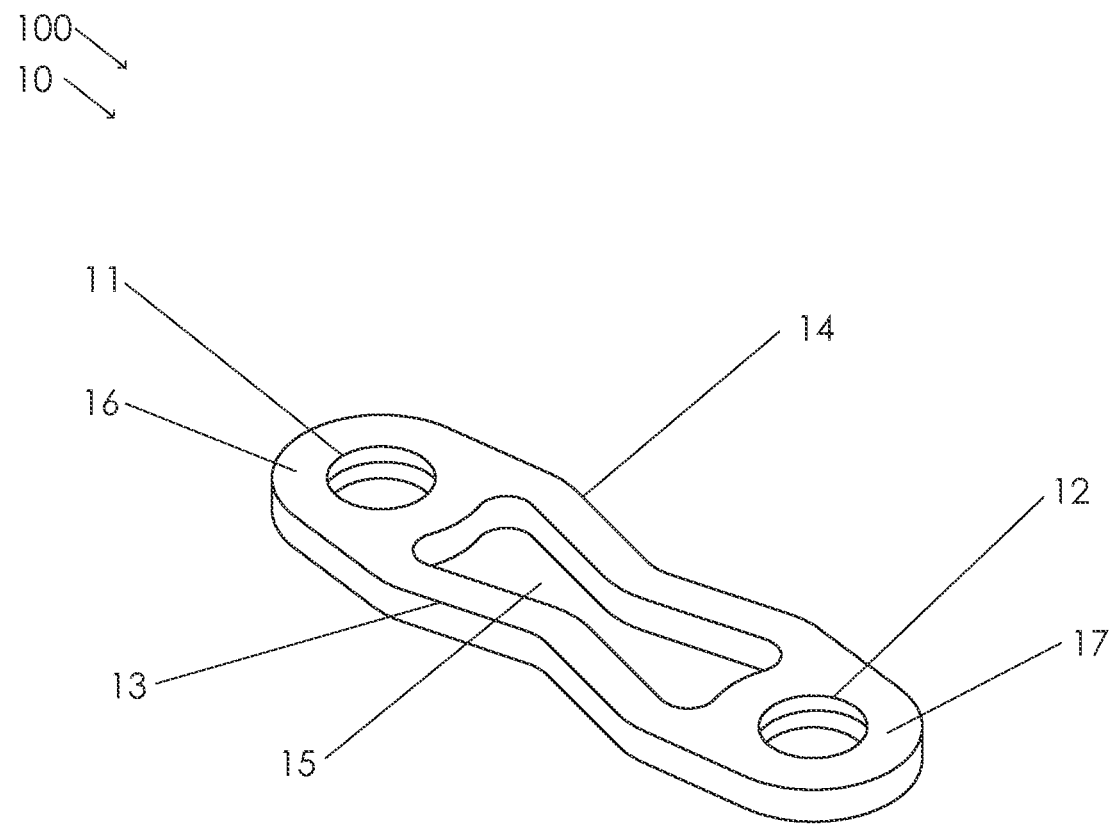
FIG. 1 provides an isometric view of a shape memory plate in an initial stretched shape.

FIG. 1 illustrates an orthopedic plate 10. The plate can be fabricated from a shape memory material such as nitinol (nickel-titanium), or any other elastic material capable of deforming and rebounding to an original shape. The plate 10 is shown in a constrained and stretched open shape 100. In the preferred embodiment, the plate 10 includes a body portion 16 defining a screw hole 11 and a body portion 17 defining a screw hole 12. Nevertheless, one of ordinary skill in the art will recognize that the plate 10 may include more or less body portions and screw holes depending upon the type of surgery. The screw holes 11 and 12, or any number of screw holes, can be smooth, tapered, or threaded as necessary to engage a screw. In the preferred embodiment, the screw holes 11 and 12 are shown with threads. The plate 10 also includes moveable arms 13 and 14 formed integrally with and between the body portions 16 and 17. Nevertheless, one of ordinary skill in the art will recognize that the plate 10 may include more moveable arms depending upon the type of surgery. The moveable arms 13 and 14 and the end portions 16 and 17 define therebetween a central opening 15, which has been elongated when the plate 10 resides in its open shape 100. The central opening 15 may be any shape, as long as it allows two or more moveable arms 13 and 14 space to move between open and compressed positions.

Figure 2:
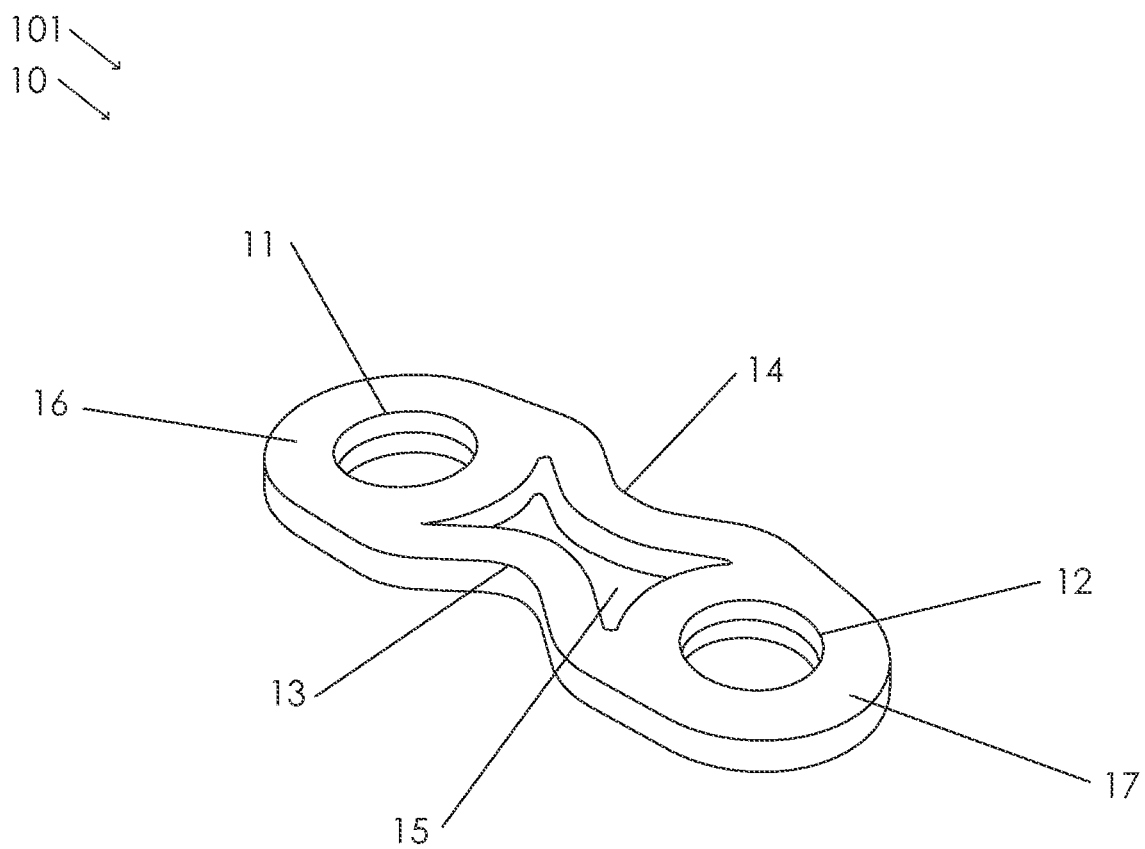
FIG. 2 provides an isometric view of the shape memory plate in a final compressed shape.

FIG. 2 illustrates the same plate 10, except in a compressed shape 101, which is the original fabrication shape of the plate 10. In this shape, the screw holes 11 and 12 can remain circular or change shape if it is desired that they bind upon screws. By application of some energy source, from room temperature, body temperature, or external, the moveable arms 13 and 14 have changed shape from the open shape 100 to the compressed shape 101. In the compressed shape 101, the moveable arms 13 and 14 have contracted and along with the end portions 16 and 17 define a central opening 15 of a different contracted shape than the elongated shape of the open shape 100.

The plate 10 begins in the compressed shape 101 and through application of an external force, the plate is moved from its compressed shape 101 to its open shape 100. In particular, the application of an external force causes the moveable arms 13 and 14 to stretch and expand, elongating the plate 10 and thus the central area 15 into the open shape 100. After application of some energy source, from room temperature, body temperature, or external, the moveable arms 13 and 14 contract and shrink, contracting the plate 10 and thus the central area 15 into the compressed shape 101.

Figure 3:
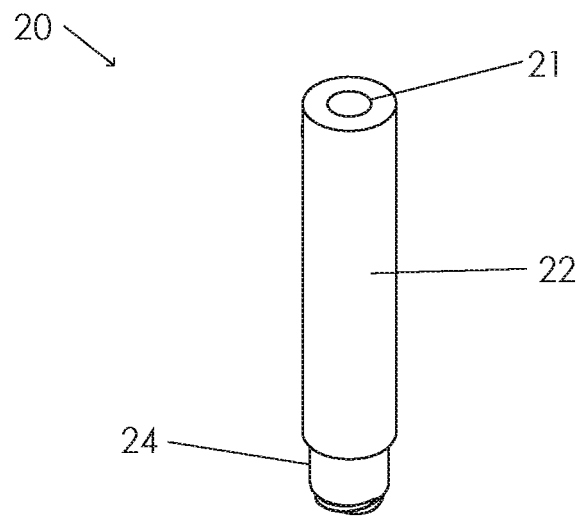
FIG. 3 provides an isometric view of a drill guide tube.
Figure 4:
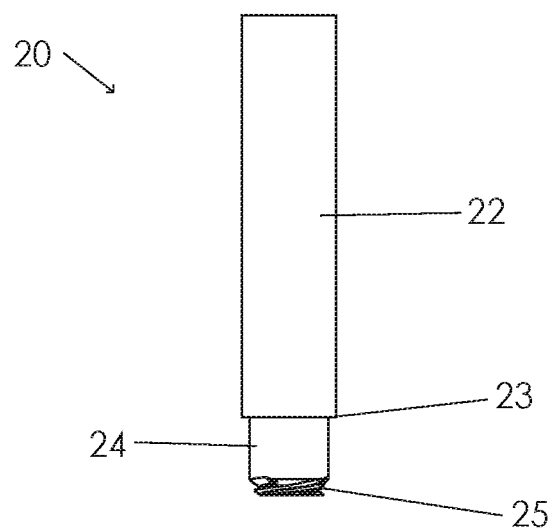
FIG. 4 provides a side view of the drill guide tube.

FIG. 3 and illustrate a drill guide tube 20. The drill guide tube 20 can be made from metal or plate, and has an inner cannulation of diameter 21 and an outer surface 22. A shoulder 23 is a location where a large outer surface 22 reduces to a new small outer surface 24 of smaller diameter. The screw threads 25 extend from the small outer surface 24, and are of the same thread characteristics needed to mate with the screw holes 11 and 12 of the plate 10.

Figure 5:
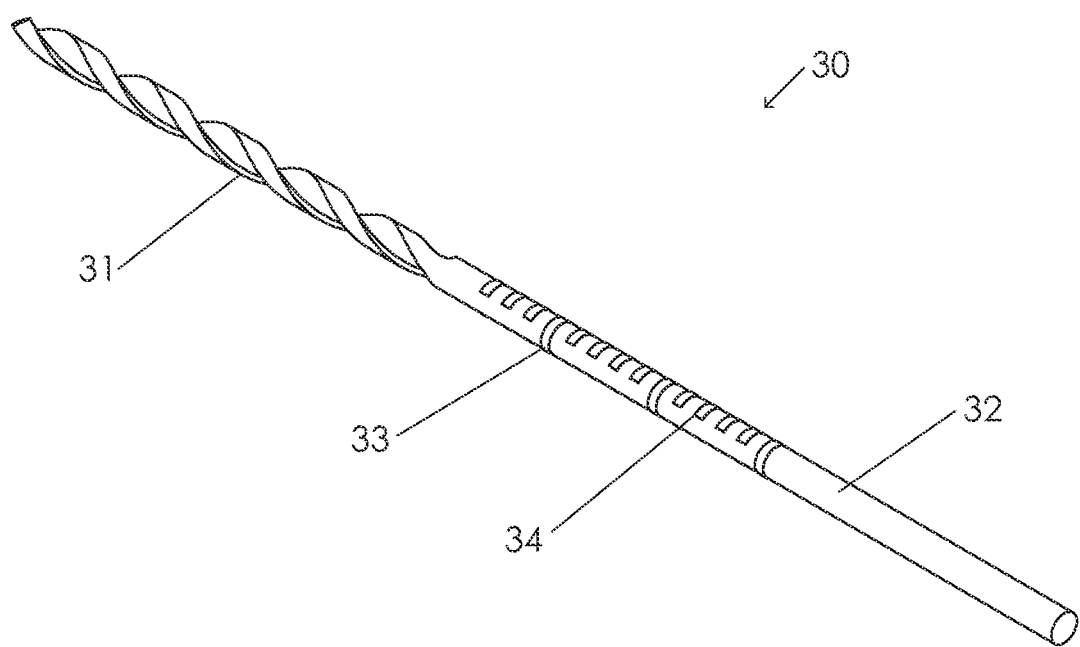
FIG. 5 provides an isometric view of a locating pin.

FIG. 5 illustrates a locating pin 30. The locating pin 30 can be manufactured of any material; in the preferred embodiment, it is made from medical grade metal. The locating pin 30 has cutting flutes 31 for cutting through bone. A shank 32 of the locating pin 30 is of a diameter that will fit into the inner cannulation 21 of the drill guide tube 20. A short sizing line 33 is an ink or engraved mark on the surface of the locating pin 30 to define a certain depth for drilling of a pilot hole. Similarly, a long sizing line 34 is also a mark for defining depth of a pilot hole, only it encircles the circumference of the locating pin 30.

Figure 6:
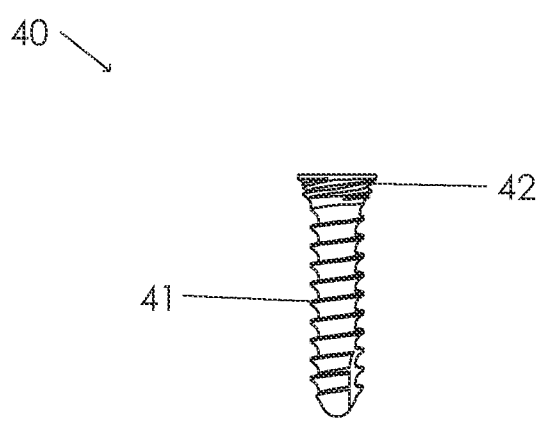
FIG. 6 provides an isometric view of a screw.

FIG. 6 illustrates a screw 40 designed to attach the plate 10 to a bone. In the preferred embodiment, the screw 40 has two threaded sections, shank threads 41 and head threads 42. The shank threads 41 are designed to engage bone once inserted into a pilot hole created by the locating pin 30. There is any number of thread characteristics related to pitch, diameter, and threads per inch that will accomplish this purpose. The head threads 42 are designed to engage the screw holes 11 and 12 of the plate 10.

Figure 7:
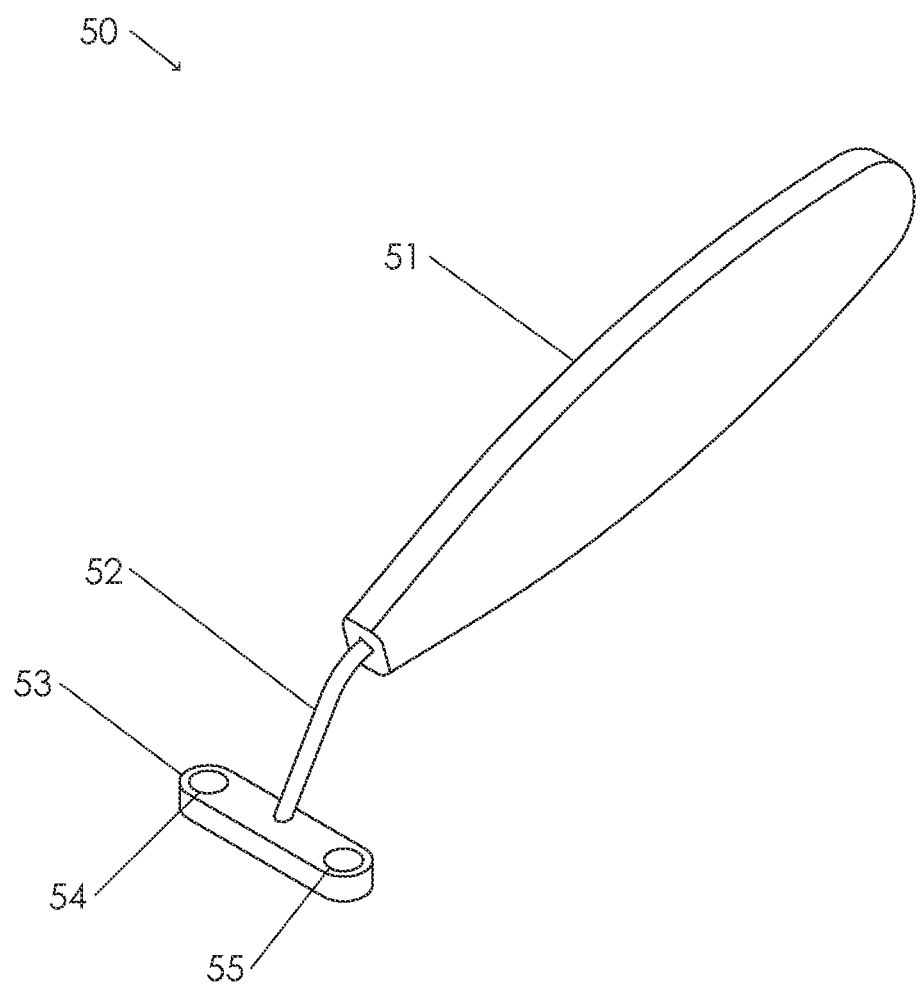
FIG. 7 provides an isometric view of an insertion tool.
Figure 8:
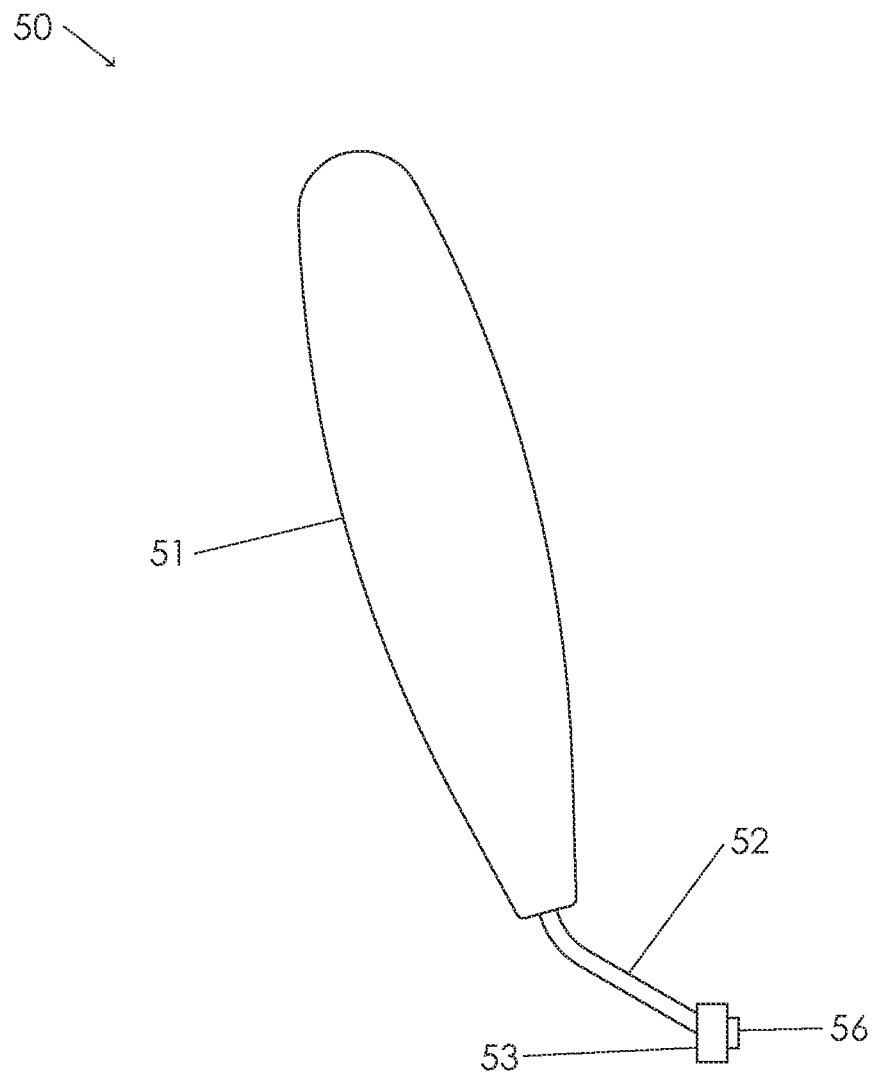
FIG. 8 provides a side view of the insertion tool.
Figure 9:
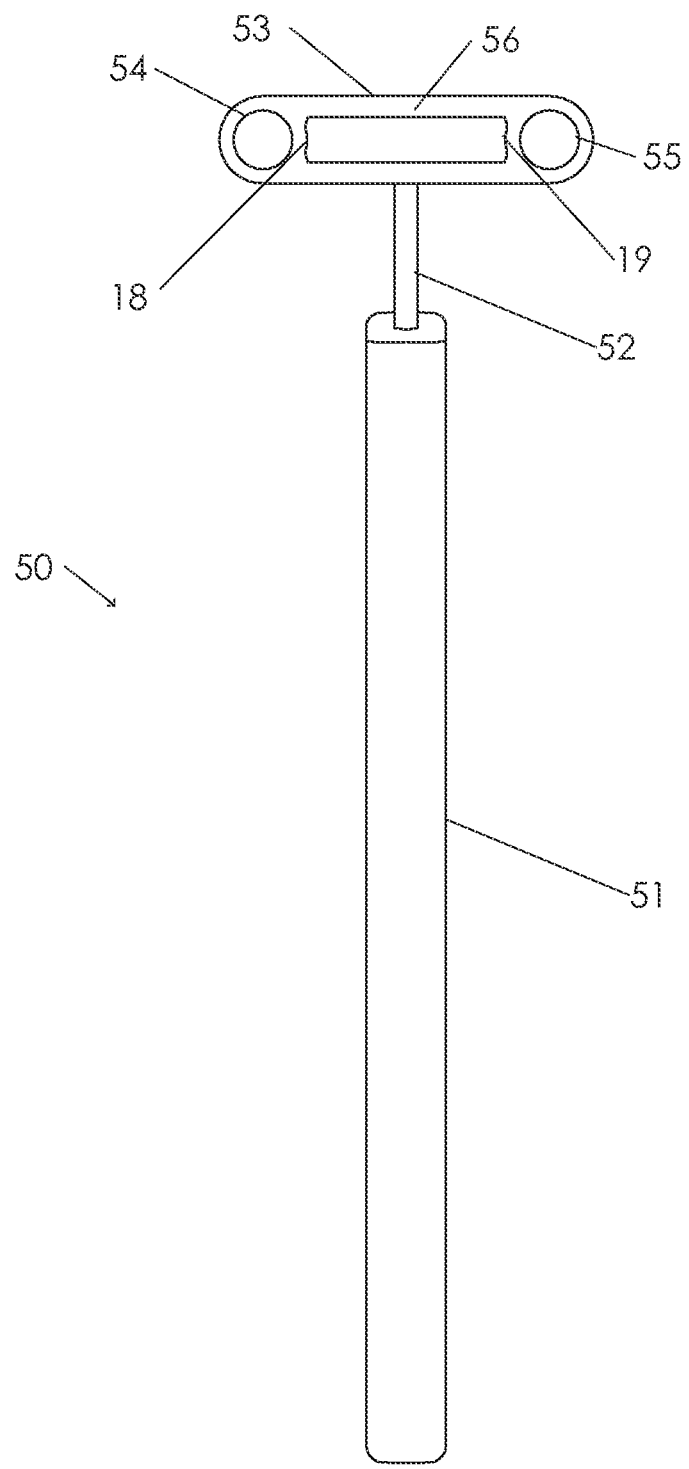
FIG. 9 provides a top view of the insertion tool.

FIGS. 7-9 illustrate an insertion tool 50. The insertion tool 50 consists of a handle 51, a shaft 52, a platform 53, and a retention spacer 56. The handle 51 can be any shape such that it ergonomically fits a surgeon's hand. The shaft 52 can be any length or angle as required to position the platform 50 on a desired bone surface. In some applications, the shaft 52 might not be needed at all, and could thus be eliminated from the insertion tool 50. The platform 53 is a solid material such as metal or plastic, designed to space drill guide holes 54 and 55 to the proper separation distance, as well as retain the plate 10 in the open shape 100. Thus, the drill guide holes 54 and 55 of the platform 53 correspond to the separation distance of the screw holes 11 and 12 of the plate 10 when it is in the open shape 100. The retention spacer 56 is designed to substantially match the length of the central opening 15 of the plate 10 when the plate 10 resides in its open shape 100, and is made from a solid material such as plastic or metal. In this preferred embodiment, the retention spacer 56 is rectangular shape. The shape of the retention spacer 56 is not critical, as long as the retention spacer 56 fits within the central opening 15 when the plate 10 resides in its open shape 100 and includes raised side portions 18 and 19 that abut the end portions 16 and 17 such that the retention spacer 56 holds the plate 10 in the open shape 100.

Figure 10:
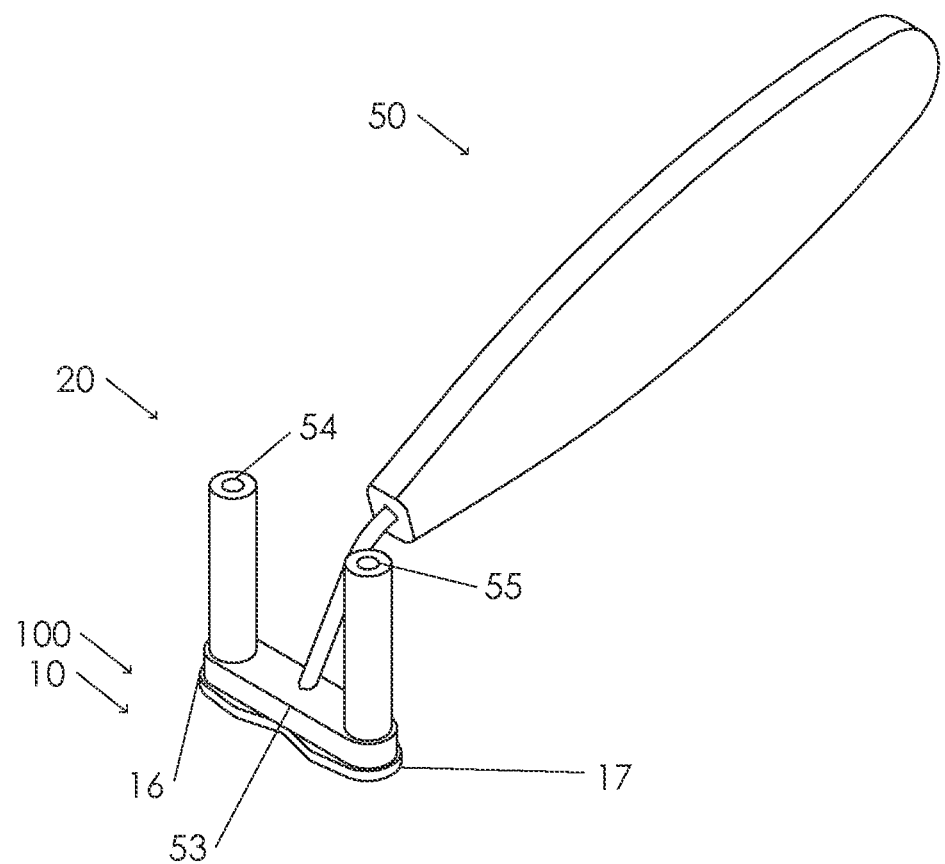
FIG. 10 provides an isometric view of the shape memory plate in its stretched shape affixed to the insertion tool with drill guide tubes in place.
Figure 11:
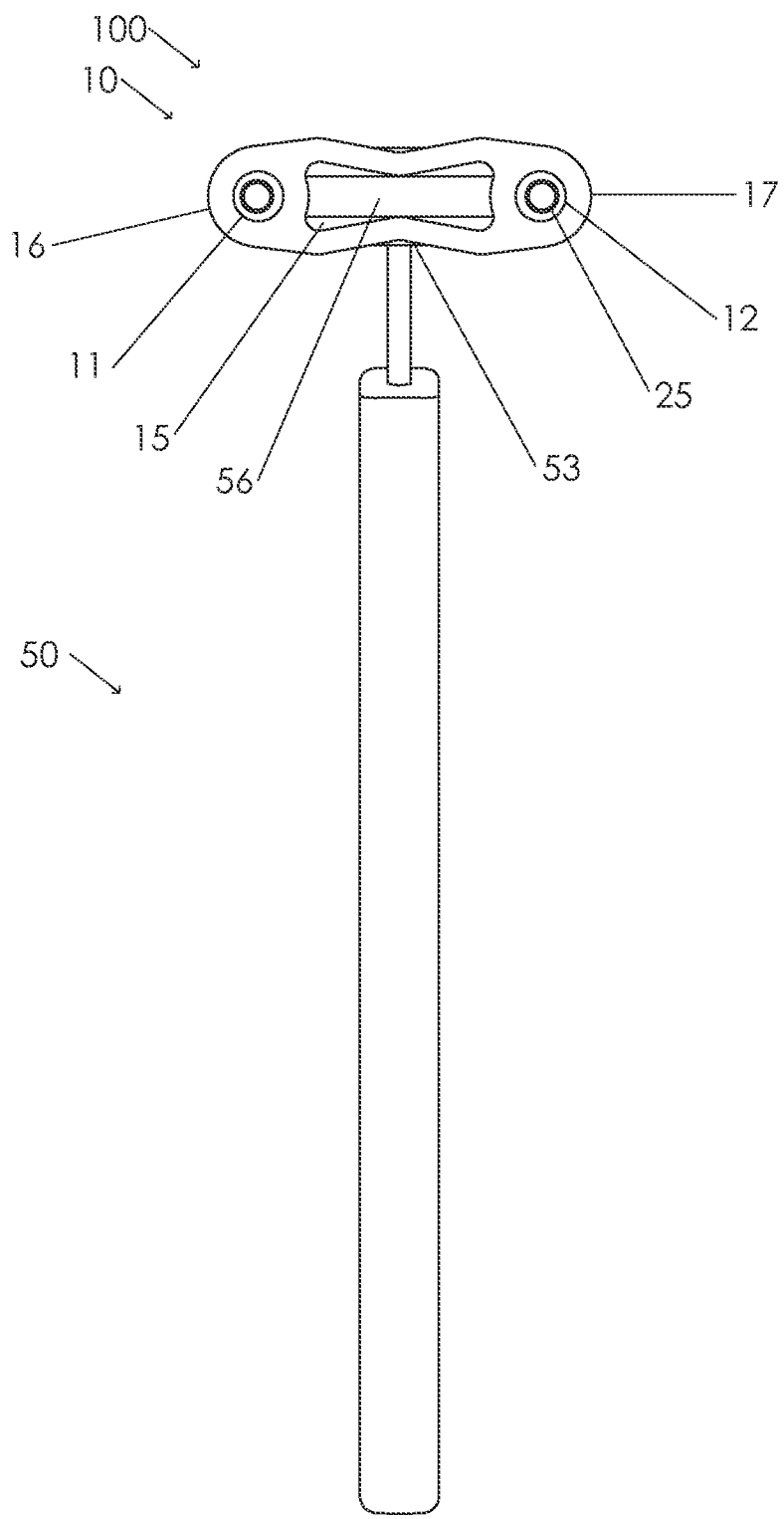
FIG. 11 provides a bottom view of a shape memory plate in a stretched shape affixed to an insertion tool with drill guide tubes in place.

FIGS. 10-11 illustrate an assembly showing the plate 10, the two drill guide tubes 20, and the plate insertion tool 50. The plate 10 is in the open shape 100 in this configuration. The small outer surface 24 of the drill guide tubes 20 pass through the drill guide holes 54 and 55 that are located on the platform 53 of the insertion tool 50. The screw threads 25 on the drill guide tubes 20 are screwed into the holes 11 and 12 of the plate 10. The retention spacer 56 is positioned in the central opening 15 of the plate 10 such that the ends of the retention spacer 56 abut the end portions 16 and 17 resulting in the retention spacer 56 maintaining the plate 10 in its open shape 100. The screw threads 25 on the drill guide tubes 20 are screwed into the holes 11 and 12 of the plate 10.

Figure 12:
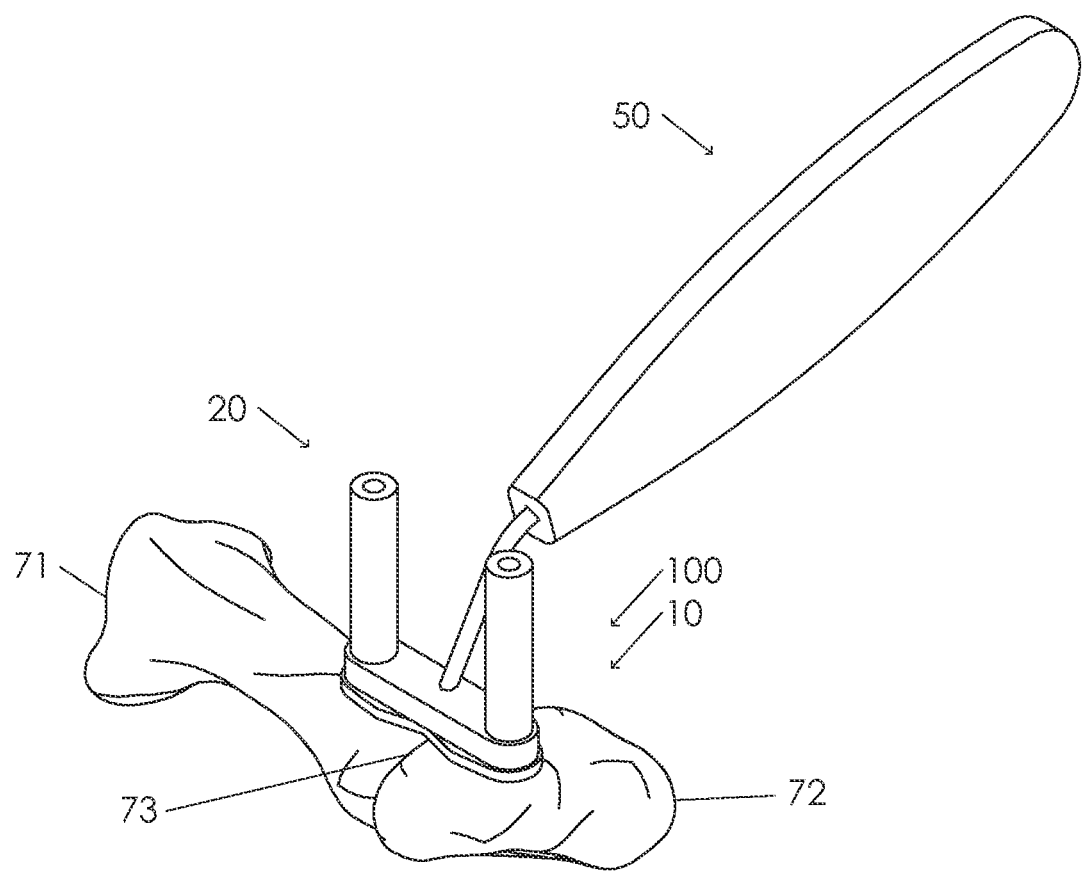
FIG. 12 provides an isometric view of the shape memory plate situated on two bones and affixed in its stretched shape to the insertion tool with drill guide tubes in place.

FIGS. 12-17 illustrate a method of use for a shape memory plate to fixate two bones or bone fragments in a surgery. The surgical procedure begins with the surgeon trying to fixate a first bone 71 and a second bone 72. As illustrated in FIG. 12, the plate 10 in the open shape 100 as a result of the insertion of the retention spacer 56 into the central opening 15 is positioned on top of a bone fusion interface 73, which lies between a first bone 71 and a second bone 72. The screw holes 11 and 12 of the plate 10 are positioned so that the screw hole 11 is over the first bone 71 and screw hole 12 is over the second bone 72. In the preferred method, the plate 10 positioned in its open shape 100 is centered over the fusion interface 73 between the first bone 71 and the second bone 72. The drill guide tubes 20 are screwed into the plate 10, passing through the platform 53 of the insertion tool 50.

Figure 13:
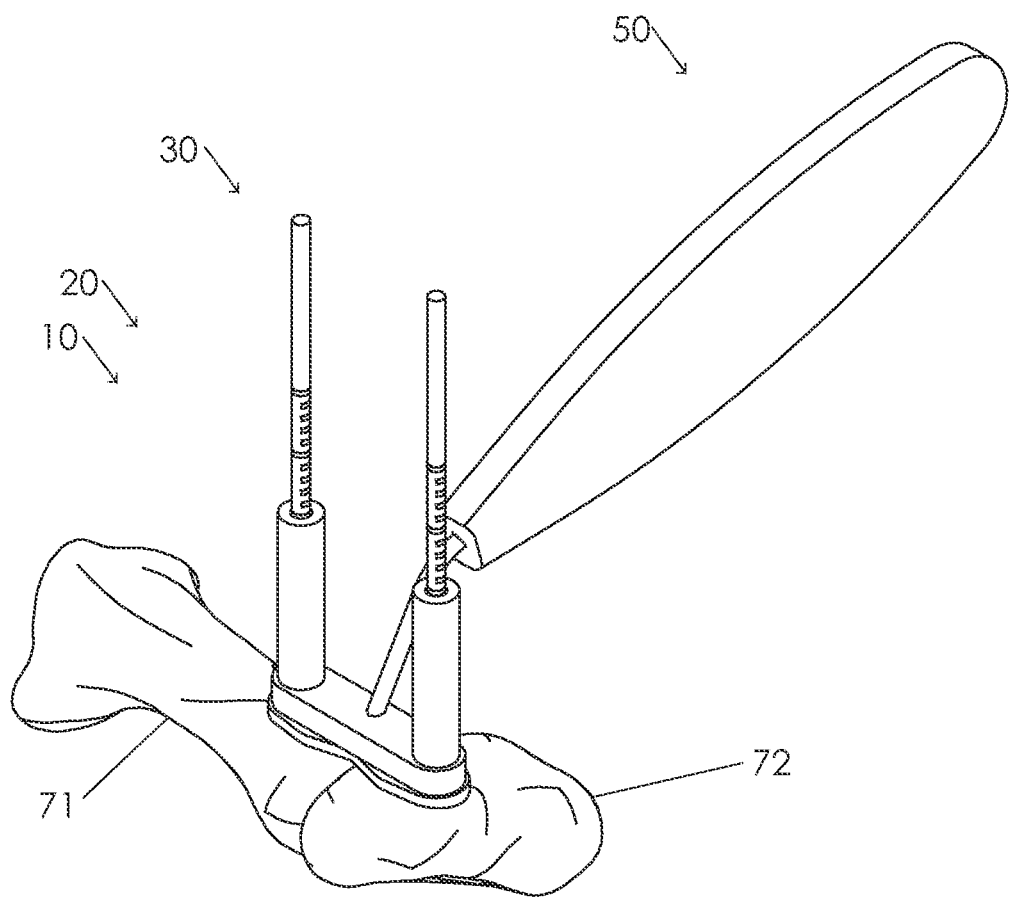
FIG. 13 provides an isometric view of the shape memory plate situated on two bones and affixed in its stretched shape to the insertion tool with drill guide tubes and locating pins in place.

After positioning the assembly as shown in FIG. 12, the surgeon uses two locating pins to temporarily anchor the plate 10 in place and measure screw lengths. As illustrated in FIG. 13, the two locating pins 30 which have been drilled into place pass through the drill guide tubes 20, through the platform 53 of the insertion tool 50, through respective screw holes 11 and 12 of the plate 10, and then into respective first and second bones 71 and 72. The short and the long sizing lines 33 and 34, respectively, can now be used to assess the depth of a screw 40 to anchor the plate 10.

Figure 14:
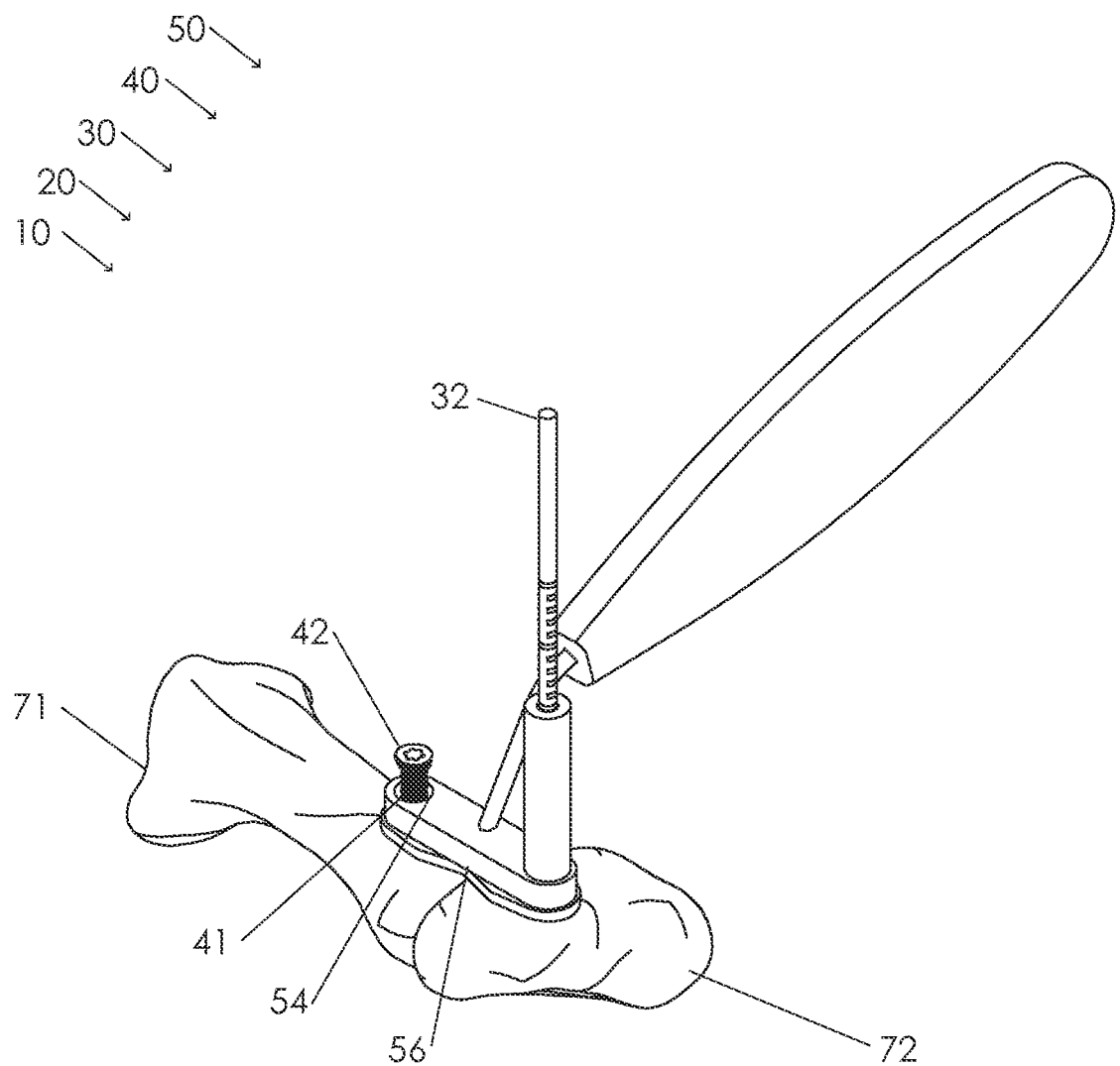
FIG. 14 provides an isometric view of the shape memory plate situated on two bones and affixed in its stretched shape to the insertion tool with one drill guide tube and locating pin in place and one screw being inserted.

At this time, the surgeon would be ready to screw the plate 10 to the first and second bones 71 and 72. As illustrated in FIG. 14, the plate 10 is positioned in its open shape 100 over the first and second bones 71 and 72 as well as centered over the fusion interface 73. One of the drill guide tube 20 remains attached to the plate 10, while the other drill guide tube 20 has been removed from the plate 10 and the platform 53 of the insertion tool 50. At this point, the insertion tool 50 remains attached to the plate 10 with the retention spacer 56 residing within the central opening 15 of plate 10. The screw 40 is screwed into the screw hole 11 of the plate 10. To reach the screw hole 11, the screw 40 passes through the screw hole 54 of the insertion tool 50. The head threads 42 of the screw 40 mate with the screw hole 11 of the plate 10. Once the screw 40 is fully in place, one side of the plate 10 will be anchored to the first bone 71.

Figure 15:
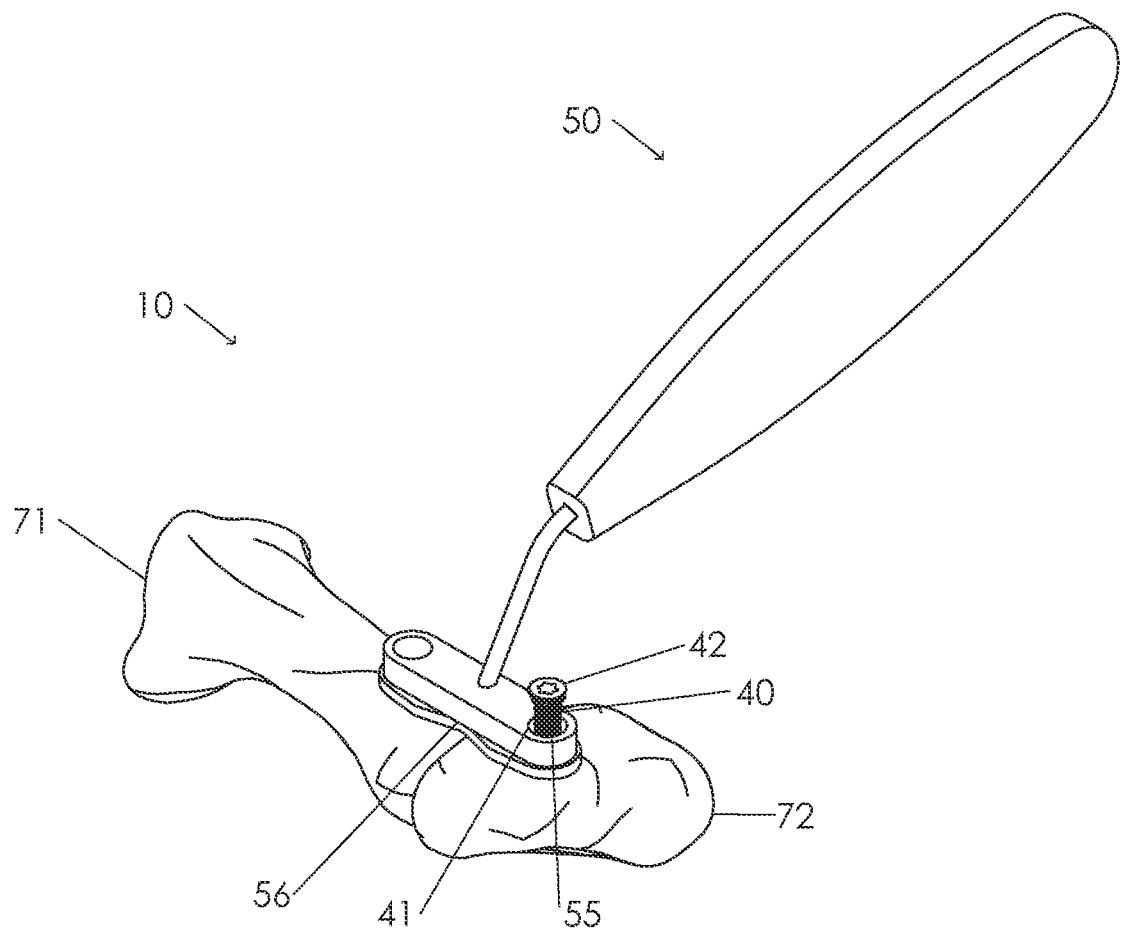
FIG. 15 provides an isometric view of the shape memory plate situated on two bones and affixed in a stretched shape affixed to the insertion tool with one screw in place and one screw being inserted.
Figure 16:
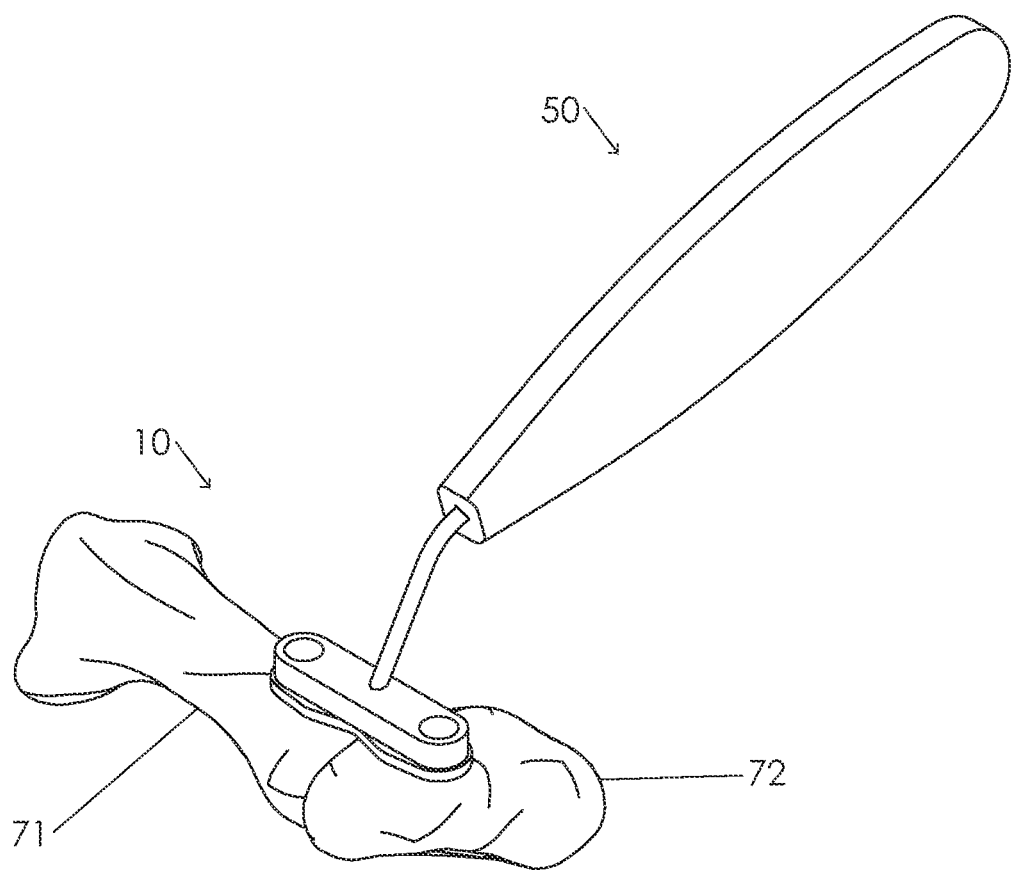
FIG. 16 provides an isometric view of the shape memory plate situated on two bones and affixed in a stretched shape to the insertion tool with two screws in place.

Referring to FIG. 15, once the first screw 40 has been screwed into place in the first bone 71, the remaining drill tube 20 is removed from the plate 10 and the platform 53 of the insertion tool 50, and a second screw 40 is screwed into the screw hole 12 of the plate 10. The second screw 40 passes through the screw hole 55 of the insertion tool 50. After both the first and second screws 40 have been screwed into place, the insertion tool 50 remains positioned relative to the plate 10 such that the retention spacer 56 is in the central opening 15 of plate 10 as illustrated in FIG. 16. The plate 10 thus is screwed to the first bone 71 and the second bone 72 and centered over the bone fusion interface 73.

Figure 17:
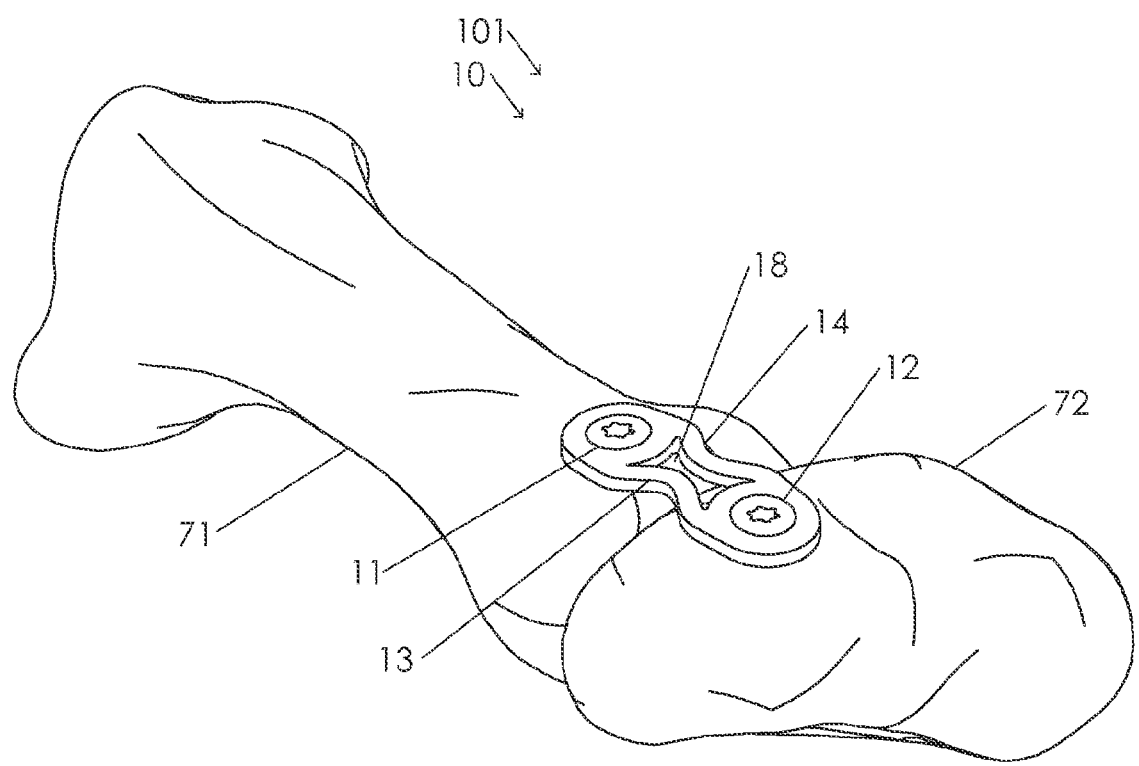
FIG. 17 provides an isometric view of the shape memory plate in its final compressed shape affixed to two bones by two screws, and released to create compression.

FIG. 17 illustrates the final step in the implantation of the plate 10 in the first bone 71 and the second bone 72. The insertion tool 50 is removed from the plate 10 due to the extraction, rotation, pulling, and/or or jiggling of the retention spacer 56 from the central opening 15 of the plate 10. The first and second screws 40 are positioned, respectively, in the screw holes 11 and 12 of the plate 10, and thus anchor the plate 10 to the first bone 71 and the second bone 72. With the retention spacer 56 removed, the shape memory plate 10 can now respond to room temperature, body temperature, or external energy input and transform in shape from its open shape 100 to its compressed shape 101. In particular, the moveable arms 13 and 14 decrease in length resulting the first central opening 15 transitioning in shape to the second new central opening 18. While the moveable arms 13 and 14 transform the plate 10 in this preferred embodiment, one of ordinary skill in the art will recognize that there are any number of designs, orientations, shapes, and numbers of moveable arms that would create the same transformation effect. Upon the transitioning of the plate 10 to its compressed shape 101, compression is created between the first bone 71 and the second bone 72 at the bone fusion location 73.

Summarizing the implantation, the surgeon selects a shape memory plate implant pre-loaded onto an insertion tool. The plate can also be pre-loaded with drill guide tubes, or those can be attached during surgery. The surgeon positions the plate at the juncture of two bones to be fused or fixated, and uses locating pins to temporarily hold the plate to the bones. The surgeon then removes one locating pin and drill guide tube, replaces it with a screw to hold one side of the plate in place, and then removes the second locating pin and drill guide tube to allow the second screw to be placed.

The ingenuity of this system is as follows. A shape memory plate that creates compression has to be held open until both sides of the plate are anchored in bone, lest the compressive force be released too early. This can be accomplished initially with an insertion tool that props open the plate. However, the plate has to be anchored to the bone before the insertion tool can be removed, to preserve the compressive force until the surgeon is ready. This then requires that the screws pass through the insertion tool in some way. The aforementioned method for implantation accomplishes these objectives. Furthermore, this method allows the surgeon to select the timing of the application of compressive force. A surgeon could potentially implant more than one plate, and leave the insertion tools in place, only to release them at the appropriate time. This sequence could allow more complex surgeries to take place. Furthermore, since the presence of the insertion tool can hide or obscure the visibility of the plate from the surgeon, the two locating pins insure that the plate remains properly oriented on the bones.

To use this shape memory plate, a medical device company or hospital could pre-load certain elements of the system prior to surgery. The shape memory plate 10 must be stretched from its compressed shape 101 shown in FIG. 2, to its open shape 100 shown in FIG. 1. The plate must then be held open via an insertion tool, such as insertion tool 50, which restrains the plate 10 in an open shape 100. This then allows for a method of preparation of the plate. Plate 10 is stretched from compressed shape 101 to open shape 100. Plate 10 is placed on insertion tool 50. Drill guides 20 can optionally be attached prior to surgery or at the time of surgery. It is also contemplated that the pre-loaded plate could be delivered in a sterile package.

Although the present invention has been described in terms of the foregoing preferred embodiment, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. A fixation system, comprising:
a plate, comprising:
   a first end portion defining a first screw hole,
   a second end portion defining a second screw hole, and
   first and second arms disposed between the first and second end portions, wherein the first and second end portions and the first and second arms define a central opening, further wherein the first and second arms expand to configure the plate in an open shape and contract to configure the plate in a compressed shape, and
an insertion tool, comprising:
   a platform including a first guide hole that aligns with the first screw hole and a second guide hole that aligns with the second screw hole when the plate is in its open shape, and
   a retention spacer adjacent the platform, the retention spacer being adapted for insertion into the central opening when the plate is in its open shape such that the retention spacer abuts the first and second end portions of the plate to retain the plate in its open shape, wherein the insertion tool allows locating of the plate for affixing a first bone and a second bone, further wherein release of the plate from the insertion tool after affixation of the plate with the first bone and the second bone allows the plate to move from its open shape to its compressed shape, thereby compressing the first bone with the second bone.

2. The fixation system according to claim 1, wherein the retention spacer comprises raised side portions that abut the first and second end portions of the plate to retain the plate in its open shape.

3. The fixation system according to claim 1, further comprising:
a first guide tube adapted to insert through the first guide hole of the platform and engage the first screw hole of the plate; and
a second guide tube adapted to insert through the second guide hole and engage the second screw hole of the plate.

4. The fixation system according to claim 3, further comprising:
a first locating pin that inserts through the first guide tube and is adapted to create a pilot hole in the first bone, wherein the first locating pin includes marks that represent depth of the first locating pin within the first bone, further wherein the first locating pin retains the plate at the first bone; and
a second locating pin that inserts through the second guide tube and is adapted to create a pilot hole in the second bone, wherein the second locating pin includes marks that represent depth of the second locating pin within the second bone, further wherein the second locating pin retains the plate at the second bone.

5. The fixation system according to claim 3, wherein:
the first screw hole includes threads, whereby the threads engage the first guide tube to maintain the first guide tube secured to the plate, further whereby, after removal of the first guide tube, the threads engage a screw inserted into the first bone to maintain the plate secured to the first bone; and
the second screw hole includes threads, whereby the threads engage the second guide tube to maintain the second guide tube secured to the plate, further whereby, after removal of the second guide tube, the threads engage a screw inserted into the second bone to maintain the plate secured to the second bone.

6. The fixation system according to claim 3, further comprising a package adapted to receive therein the plate coupled with the insertion tool such that the insertion tool retains the plate in its open shape and the first and second guide tubes remain coupled with the plate.

7. The fixation system according to claim 6, wherein the package maintains the plate, the insertion tool, and the first and second guide tubes sterile after sterilization of the fixation system.

8. The fixation system according to claim 1, further comprising a package adapted to receive therein the plate coupled with the insertion tool such that the insertion tool retains the plate in its open shape.

9. The fixation system according to claim 8, wherein the package maintains the plate and the insertion tool sterile after sterilization of the fixation system.

10. A method for affixing bones, comprising
a. providing a plate, comprising:
   a first end portion defining a first screw hole,
   a second end portion defining a second screw hole, and
   first and second arms disposed between the first and second end portions, wherein the first and second end portions and the first and second arms define a central opening, further wherein the first and second arms expand to configure the plate in an open shape and contract to configure the plate in a compressed shape;
b. providing an insertion tool, comprising:
   a platform including a first guide hole and a second guide hole, and
   a retention spacer adjacent the platform;
c. moving the plate from its compressed shape to its open shape;
d. inserting the retention spacer of the insertion tool into central opening of the plate, wherein the retention spacer abuts the first and second end portions of the plate to retain the plate in its open shape, further wherein the first guide hole aligns with the first screw hole and the second guide hole aligns with the second screw hole;
e. engaging a first drill guide tube with the first screw hole of the first plate and a second drill guide tube with the second screw hole of the plate;
f. placing the plate onto first and second bones requiring fixation using the insertion tool;
g. inserting a first locating pin through the first drill guide tube and drilling the first locating pin into the first bone;
h. inserting a second locating pin through the second drill guide tube and drilling the second locating pin into the second bone;
i. removing the first locating pin from the first drill guide tube and the first drill guide tube from the plate;
j. inserting a first screw through the first screw hole of the plate and into the first bone;
k. removing the second locating pin from the second drill guide tube and the second drill guide tube from the plate;
l. inserting a second screw through the second screw hole of the plate and into the second bone;
m. decoupling the insertion tool from the plate such that the plate moves to its compressed shape.

11. A The method for affixing bones, comprising:
a. coupling a first plate configurable between an open shape and a compressed shape with a first insertion tool such that the first insertion tool maintains the plate in its open shape;
b. engaging a first drill guide tube with a first screw hole of the first plate and a second drill guide tube with a second screw hole of the first plate;

c. coupling a second plate configurable between an open shape and a compressed shape with a second insertion tool such that the second insertion tool maintains the second plate in its open shape;
d. engaging a third drill guide tube with a first screw hole of the second plate and a fourth drill guide tube with a second screw hole of the second plate;
e. placing the first plate onto first and second bones requiring fixation using the first insertion tool;
f. inserting a first locating pin through the first drill guide tube and drilling the first locating pin into the first bone;
g. inserting a second locating pin through the second drill guide tube and drilling the second locating pin into the second bone;
h. removing the first locating pin from the first drill guide tube and the first drill guide tube from the first plate;
i. inserting a first screw through the first screw hole of the first plate and into the first bone;
j. removing the second locating pin from the second drill guide tube and the second drill guide tube from the first plate;
k. inserting a second screw through the second screw hole of the first plate and into the second bone;
l. placing the second plate onto the first and second bones requiring fixation using the second insertion tool;
m. inserting a third locating pin through the third drill guide tube and drilling the third locating pin into the first bone;
n. inserting a fourth locating pin through the fourth drill guide tube and drilling the fourth locating pin into the second bone;
o. removing the third locating pin from the third drill guide tube and the third drill guide tube from the second plate;
p. inserting a third screw through the first screw hole of the second plate and into the first bone;
q. removing the fourth locating pin from the fourth drill guide tube and the fourth drill guide tube from the second plate;
r. inserting a fourth screw through the second screw hole of the second plate and into the second bone;
s. decoupling the first insertion tool from the first plate and the second insertion tool from the second plate such that the first and second plates move to their compressed shapes.

12. The method for affixing bones according to claim 11, wherein coupling a first plate with a first insertion tool and coupling a second plate with a second insertion tool comprises:
providing a first and a second plate, each plate comprising:
a first end portion defining the first screw hole,
a second end portion defining the second screw hole, and
first and second arms disposed between the first and second end portions, wherein the first and second end portions and the first and second arms define a central opening, further wherein the first and second arms expand to configure the plate in its open shape and contract to configure the plate in its compressed shape;
providing a first insertion tool and a second insertion tool, each insertion tool comprising:
a platform including a first guide hole and a second guide hole, and
a retention spacer adjacent the platform;
moving the first plate from its compressed shape to its open shape;
inserting the retention spacer of the first insertion tool into the central opening of the first plate, wherein the retention spacer abuts the first and second end portions of the first plate to retain the first plate in its open shape, further wherein the first guide hole aligns with the first screw hole and the second guide hole aligns with the second screw hole;
moving the second plate from its compressed shape to its open shape; and
inserting the retention spacer of the second insertion tool into the central opening of the second plate, wherein the retention spacer abuts the first and second end portions of the second plate to retain the second plate in its open shape, further wherein the first guide hole aligns with the first screw hole and the second guide hole aligns with the second screw hole.

13. A method for a fixation system, comprising:
providing a plate, comprising:
a first end portion defining a first screw hole,
a second end portion defining a second screw hole, and
first and second arms disposed between the first and second end portions, wherein the first and second end portions and the first and second arms define a central opening further wherein the first and second arms expand to configure the plate in an open shape and contract to configure the plate in a compressed shape;
providing an insertion tool, comprising:
a platform including a first guide hole and a second guide hole, and
a retention spacer adjacent the platform;
moving the plate from its compressed shape to its open shape; and
inserting the retention spacer of the insertion tool into the central opening of the plate, wherein the retention spacer abuts the first and second end portions of the plate to retain the plate in its open shape, further wherein the first guide hole aliens with the first screw hole and the second guide hole aligns with the second screw hole.

14. The method for a fixation system according to claim 13, further comprising packaging the plate loaded on the insertion tool such that the insertion tool retains the plate in its open position.

15. The method for a fixation system according to claim 13, further comprising affixing two drill guide tubes to the plate.

16. The method for a fixation system according to claim 15, further comprising packaging the plate loaded on the insertion tool such that the insertion tool retains the plate in its open position and the first and second guide tubes remain affixed with the plate.

* * * * *